(12) United States Patent
Heckroth et al.

(10) Patent No.: US 11,247,925 B2
(45) Date of Patent: Feb. 15, 2022

(54) BIODEGRADATION OF ANILINE FROM HYPERSALINE ENVIRONMENTS USING HALOPHILIC MICROORGANISMS

(71) Applicant: Covestro Deutschland AG, Leverkusen (DE)

(72) Inventors: Heike Heckroth, Odenthal (DE); Christoph Herwig, Vienna (AT); Donya Kamravamanesh, Vienna (AT)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 16/476,909

(22) PCT Filed: Jan. 9, 2018

(86) PCT No.: PCT/EP2018/050431
§ 371 (c)(1),
(2) Date: Jul. 10, 2019

(87) PCT Pub. No.: WO2018/130510
PCT Pub. Date: Jul. 19, 2018

(65) Prior Publication Data
US 2019/0352205 A1 Nov. 21, 2019

(30) Foreign Application Priority Data
Jan. 10, 2017 (EP) ..................... 17150752

(51) Int. Cl.
*C02F 3/34* (2006.01)
*C02F 1/461* (2006.01)
(Continued)

(52) U.S. Cl.
CPC .............. *C02F 3/346* (2013.01); *C02F 1/461* (2013.01); *C02F 3/02* (2013.01); *C02F 2101/38* (2013.01);
(Continued)

(58) Field of Classification Search
None
See application file for complete search history.

(56) References Cited

U.S. PATENT DOCUMENTS

2010/0219372 A1\* 9/2010 Hook ........................ C01D 3/16
252/182.32
2010/0261255 A1\* 10/2010 Pereira ..................... C02F 3/104
435/252.1
(Continued)

FOREIGN PATENT DOCUMENTS

| WO | 2007/130851 A2 | 11/2007 |
| WO | 2009/026208 A2 | 2/2009 |
| WO | 2009/026211 A2 | 2/2009 |

OTHER PUBLICATIONS

Wyndham, Evolved Aniline Catabolism in Acinetobacter calcoaceticus during Continuous Culture of River Water, Applied and Environmental Microbiology, Apr. 1986, p. 781-789, does not discuss catabolism of aniline in hypersaline media. (Year: 1986).\*
(Continued)

*Primary Examiner* — Chester T Barry
(74) *Attorney, Agent, or Firm* — Faegre Drinker Biddle & Reath LLP

(57) ABSTRACT

The present invention relates to a method for reducing the aniline content of hypersaline wastewater, said method comprising the steps of (a) providing a composition A comprising hypersaline wastewater and aniline, and (b) contacting composition A with cells of at least one halophilic microbial strain, thereby generating a composition B comprising said composition A and cells of said at least one halophilic microbial strain. The present invention further concerns a method for the production of chlorine and sodium hydroxide. Further encompassed by the present
(Continued)

Figure 1:
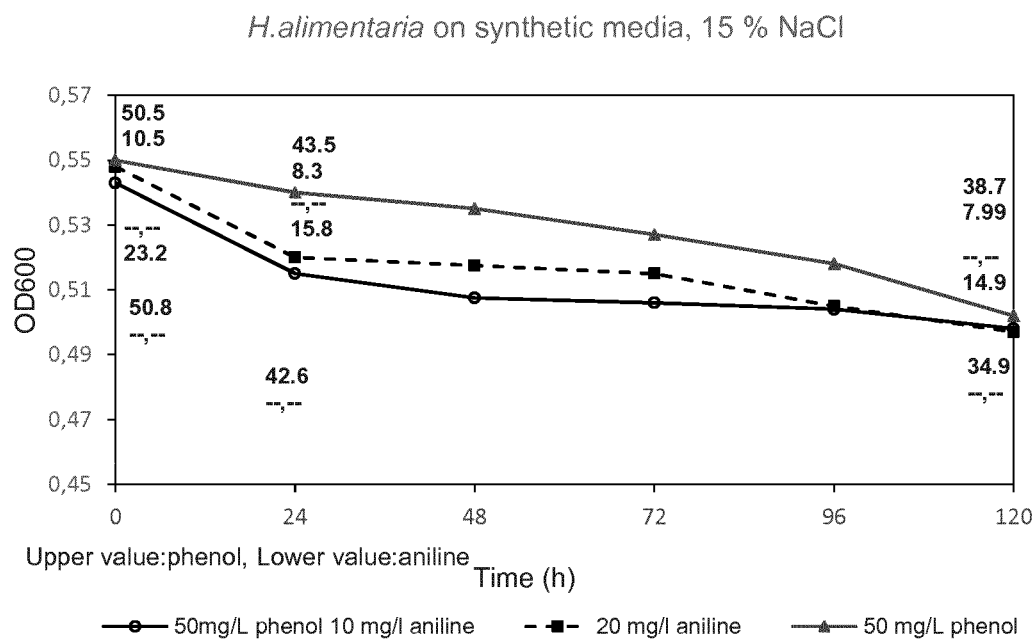

invention is a composition comprising hypersaline wastewater, aniline, and cells of at least one halophilic microbial strain.

18 Claims, 4 Drawing Sheets

(51) Int. Cl.
    *C02F 3/02*         (2006.01)
    *C02F 101/38*      (2006.01)
    *C02F 103/08*      (2006.01)
    *C02F 103/36*      (2006.01)
(52) U.S. Cl.
    CPC ...... *C02F 2103/08* (2013.01); *C02F 2103/36* (2013.01); *C02F 2305/06* (2013.01)

(56) References Cited

U.S. PATENT DOCUMENTS

| | | | | |
|---|---|---|---|---|
| 2011/0008469 | A1* | 1/2011 | Barreto | A01N 33/04 424/719 |
| 2019/0309889 | A1* | 10/2019 | Mogensen | A01N 59/00 |
| 2019/0352205 | A1* | 11/2019 | Heckroth | C02F 3/02 |

OTHER PUBLICATIONS

Emerson, Haloferax sp. D1227, a halophilic Archaeon capable of growth on aromatic compounds, Arch Microbiol (1994) 161:445-452 (Year: 1994).*
Fukumori, Nucleotide Sequences and Regulational Analysis of Genes Involved in Conversion of Aniline to Catechol in Pseudomonas putida UCC22(pTDN1), J. Bacteriology, Jan. 1997, p. 399-408 (Year: 1997).*
Cuadros-Orellana, "Isolation and Characterization of halophilic archaea able to grow in aromatic compounds," Intl Biodeterioration & Biodegradation, 57 (2006) 151-154 (Year: 2006).*
Davli, "*Arhodomonas* sp. Strain Seminole and Its Genetic Potential To Degrade Aromatic Compounds Under High-Salinity Conditions," Applied and Environmental Microbiology, Nov. 2014, vol. 80 No. 21, p. 6664-6676 (Year: 2014).*
Fathepure, "Recent studies in microbial degradation of petroleum hydrocarbons in hypersaline environments," Frontiers in Microbiology, Apr. 2014, vol. 5 Article 173, p. 1-16 (Year: 2014).*
Azachi et al., Transformation of formaldehyde by a *Halomonas* sp., Can J Microbiol., vol. 41, 1995, p. 548-553 (Year: 1995).*
O'Neill, F.J & Bromley-Challenor, Katie & Greenwood, R.J & Knapp, J.S. (2000). Bacterial growth on aniline: Implications for the biotreatment of industrial wastewater. Water Research. 34. 4397-4409. 10.1016/S0043-1354(00)00215-3. (Year: 2000).*
International Preliminary Report on Patentability received for PCT Patent Application No. PCT/EP2018/050431, dated Jul. 25, 2019, 10 pages.
International Search Report and Written Opinion received for PCT Patent Application No. PCT/EP2018/050431, dated Mar. 22, 2018, 14 pages.
Li et al., "Isolation and Characterization of Aniline Degradation Slightly Halophilic Bacterium, *Erwinia* Sp. Strain HSA 6", Microbiological Research, vol. 165, No. 5, Jul. 20, 2010, pp. 418-426.
Azachi et al., "Transformation Of Formaldehyde By A Halomonas SP.", Canadian Journal of Microbiology, vol. 41, No. 6, Jun. 1995, pp. 548-553.
Campo et al., "Aerobic Biodegradation Of Amines In Industrial Saline Wastewaters", Chemosphere, vol. 85, No. 7, Nov. 2011, pp. 1199-1203.
Elham et al., "The Study Of Organic Removal Efficiency And Halophilic Bacterial Mixed Liquor Characteristics In A Membrane Bioreactor Treating Hypersaline Produced Water At Varying Organic Loading Rates", Bioresource Technology, vol. 149, Dec. 2013, pp. 486-495.
Fu et al., "Degradation Of 3-Phenylpropionic Acid By Haloferax sp.D122", Extremophiles, vol. 3, 1999, pp. 45-53.
Jin et al., "Biodegradation Of Aniline In An Alkaline Environment By A Novel Strain Of The Halophilic Bacterium, Dietzia Natronolimnaea JQ-AN", Bioresource Technology, vol. 117, Aug. 2012, pp. 148-154.
O'Neill F. J. et al., "Bacterial Growth On Aniline: Implications For The Biotreatment Of Industrial Wastewater", Water Research, vol. 34, No. 18, Dec. 15, 2000, pp. 4397-4409.
Yoon et al., "*Halomonas Alimentaria* sp. Nov., Isolated From Jeotgal, A Traditional Korean Fermented Seafood", International Journal Of Systematic And Evolutionary Microbiology, vol. 52, No. 1, 2002, pp. 123-130.

\* cited by examiner

BIODEGRADATION OF ANILINE FROM HYPERSALINE ENVIRONMENTS USING HALOPHILIC MICROORGANISMS

CROSS-REFERENCE TO RELATED APPLICATIONS

This application is a national stage application (under 35 U.S.C. § 371) of PCT/EP2018/050431, filed Jan. 9, 2018, which claims benefit of European Application No. 17150752.8, filed Jan. 10, 2017, both of which are incorporated herein by reference in their entirety.

The present invention relates to a method for reducing the aniline content of hypersaline wastewater, said method comprising the steps of (a) providing a composition A comprising hypersaline wastewater and aniline, and (b) contacting composition A with cells of at least one halophilic microbial strain, thereby generating a composition B comprising said composition A and cells of said at least one halophilic microbial strain. The present invention further concerns a method for the production of chlorine and sodium hydroxide. Further encompassed by the present invention is a composition comprising hypersaline wastewater, aniline, and cells of at least one halophilic microbial strain.

Aniline is the major industrial chemical intermediate which is used in the manufacturing of herbicides, developers, perfumes, medicine, rubber and dyes. Due to its expanded use in industry, growing amounts of aniline are being released into the soil and water bodies, posing an environmental threat and health risk to living organisms. Several physical and chemical methods for example sorption, ozonation and electrochemical treatment are used to treat aniline-containing salty residual streams. Most of the mentioned treatments are not able to reduce the total organic carbon content in the salty residual streams down to the required maximum level. Development of a viable alternative biological process is of increasing interest owing to its cost effectiveness and environmental benefit.

Hypersaline solutions are an important material for the chloralkali process which is an industrial process for the electrolysis of NaCl. It is the technology used to produce chlorine and sodium hydroxide. However, very pure hypersaline solutions are needed. Therefore, it is difficult to use recycled hypersaline wastewater for the chloralkali process. For example, hypersaline wastewater from methylene diamine production contains aniline which shall be removed prior to subjecting the wastewater to the chloralkali process. The same applies to formate which can be found in many industrial wastewaters. E.g. hypersaline wastewater from methylene diamine production contains about 300-500 mg/l formate which has to be removed, otherwise chlorine will be contaminated with $CO_2$.

Biodegradation of aniline is previously reported using various bacterial species of *Pseudomonas, Comamonas, Acinetobacter, Rhodococcus, Frateuria, Moraxella, Delftia, Nocardia* and *Dietzia*. These bacteria biodegraded aniline under moderate conditions (see below). Also, formate can be degraded by certain microbial cells, e.g. by enzymes such as formate dehydrogenases. However, aniline and/or formate-containing residual streams frequently have elevated salinity and treatment of hypersaline residual streams represents a challenge since high salt concentration disrupts bacteria metabolism present in normal biological treatment systems. Also using normal bacteria for hypersaline residual streams requires prior dilutions to lower salinity with fresh water if available at all.

WO 2013/124375 discloses the reduction of total organic carbon by certain halophilic and/or haloalkaliphilic microorganisms.

Woolard and Irvine (1995) disclose the treatment of hypersaline wastewater in the sequencing batch reactor (Woolard and Irvine. Treatment of hypersaline wastewater in the sequencing batch reactor. Water Research 29.4 (1995): 1159-1168).

Azachi et al. (1995) disclose the isolation of a halotolerant Gram-negative *eubacterium* from soil collected at a storage site for formaldehyde (Azachi, M, et al. Transformation of formaldehyde by a *Halomonas* sp. Canadian journal of microbiology 41.6 (1995): 548-553).

Schnell et al. (1989) reported the anaerobic degradation of aniline to $CO_2$ and $NH_3$ using *Desulfobacterium D. anilini* (Schnell, S, et al. (1989). Anaerobic degradation of aniline and dihydroxybenzenes by newly isolated sulfate-reducing bacteria and description of Desulfobacterium anilini. Archives of Microbiology, 152(6), 556-563).

Gua Xia Zhang et al. (2011) disclosed a *Rhizobium borbori* sp. isolated from activated sludge that was capable of aniline degradation in presence of 2% NaCl (Zhang, G X, et al. *Rhizobium borbori* sp. nov., aniline-degrading bacteria isolated from activated sludge. International journal of systematic and evolutionary microbiology 61.4 (2011): 816-822).

Junmin Li et al. (2009) reported that the slightly halophilic *Erwinia* sp. strain HSA6 tolerated up to 6% NaCl and 3 g/l aniline. Aniline in a concentration of 0.5% was degraded after 24 hours using *Erwinia* sp. strain HSA6 (Li, J, et al. Isolation and characterization of aniline degradation slightly halophilic bacterium, *Erwinia* sp. Strain HSA 6. Microbiological research 165.5 (2010): 418-426).

Jin et al. (2012) disclosed the biodegradation of aniline in alkaline environment pH 8.0 and up to 6% NaCl by *Dietzia natronolimnaea* JQ-AN. 87% of 300 mg/l aniline was degraded after 120 hours of incubation in the presence of acetate (Jin, Q, et al. Biodegradation of aniline in an alkaline environment by a novel strain of the halophilic bacterium, *Dietzia natronolimnaea* JQ-AN. Bioresource technology 117 (2012): 148-154).

Liu et al. (2002) reported the degradation of aniline of up to 5000 mg/l in 7 days by *Delfina* sp. AN3 (Liu, Z, et al. Degradation of aniline by newly isolated, extremely aniline-tolerant *Delftia* sp. AN3. Applied microbiology and biotechnology 58.5 (2002): 679-682).

F. J. O'Neill et al. (2000) showed that a bacterial consortium was capable of aerobic, fermentative degradation of aniline (260 mgfl) in 0.2 and 4% NaCl concentration and pH of 5 to 7 (O'neill, F J, et al. Bacterial growth on aniline: implications for the biotreatment of industrial wastewater. Water Research 34.18 (2000): 4397-4409).

Ahmed et al. (2010) disclosed that *Staphylococcus aureus* STI had a tolerance of up to 2000 ppm aniline. Preferred growth conditions included 700 ppm aniline and the presence of glucose (Ahmed, S, et al. Isolation and characterization of a bacterial strain for aniline degradation. African Journal of Biotechnology (2010) 9.8).

Oren et al. (1992) showed that transformation of nitrophenols to aminophenols could be done by *Haloanaerobium praevalens* and *Sporohalobacter marismortui*. Degradation of 25 ppm aniline was observed under anaerobic conditions (Oren, A, et al. Microbial degradation of pollutants at high salt concentrations. Biodegradation 3.2-3 (1992): 387-398).

Campo et al. (2011) is concerned with an activated sludge from soil contaminated with aromatic compounds. Aerobic biodegradation of amines such as aniline and MDA was observed up to 5 mg/l aniline (Campo, P, et al. Aerobic biodegradation of amines in industrial saline wastewaters. Chemosphere 85.7 (2011): 1199-1203).

Emerson et al. (1994) reported the isolation of a pink-pigmented halophilic Archaeon, *Haloferax* sp. D1227, from soil contaminated with oil brine. *Haloferax* strain D1227 was shown to be able to use aromatic substrates as sole carbon and energy sources for growth (Emerson, D, et al. *Haloferax* sp. D1227, a halophilic Archaeon capable of growth on aromatic compounds. Archives of microbiology 161.6 (1994): 445-452).

Zhuang et al. (2007) reported the isolation of aniline-degrading *Rhodococcus* sp. strain AN5 by selective enrichment culturing on a minimum salt medium (MSM). The optimal conditions for aniline biodegradation by *Rhodococcus* sp. strain AN5 were 30° C. and pH 7.0 (Zhuang, R, et al. Isolation and characterization of aniline-degrading *Rhodococcus* sp. strain AN5 Journal of Environmental Science and Health Part A 42.13 (2007): 2009-2016). A review from Zhuang (2010) summarizes the progress in decontamination by halophilic microorganisms in saline wastewater and soil (Zhuang, X, et al. Progress in decontamination by halophilic microorganisms in saline wastewater and soil. Environmental pollution 158.5 (2010): 1119-1126).

A further review on decontamination of organic pollutants was published by Le Borgne (Le Borgne et al. Biodegradation of organic pollutants by halophilic bacteria and archaea. Journal of molecular microbiology and biotechnology 15.2-3 (2008): 74-92).

Wyndham (1986) discloses that *Acinetobacter calcoaceticus* were able to grow at concentrations of aniline greater than 16 mM (Wyndham, R C, Evolved aniline catabolism in *Acinetobacter calcoaceticus* during continuous culture of river water. Applied and environmental microbiology 51.4 (1986): 781-789).

Fu and Oriel (1998) reported the purification of gentisate 1,2-dioxygenase from the extreme halophile *Haloferax* sp. D1227. *Haloferax* sp. D1227 was the first halophilic archeon to demonstrate the utilization of aromatic compounds as sole carbon and energy sources for growth. The optimal salt concentration, temperature, and pH for the activity of gentisate 1,2-dioxygenase were 2M KCL or NaCl, 45° C., and pH 7.2, respectively (Fu, W, and Oriel, P. Gentisate 1,2-dioxygenase from *Haloferax* sp. D1227. Extremophiles 2.4 (1998): 439-446).

Fu and Oriel (1999) further reported the degradation of 3-phenylpropionic acid by *Haloferax* sp. D1227 (Fu, W, and Oriel, P. Degradation of 3-phenylpropionic acid by *Haloferax* sp. D1227. Extremophiles 3.1 (1999): 45-53).

Fathepure (2014) briefly reviewed recent studies in microbial degradation of petroleum hydrocarbons in hypersaline environments. The authors reported that members of the genera *Halomonas Alcanivorax, Marinobacter, Haloarcula,* and *Halobacterium* dominate the published literature. However, although studies have reported degradation of polycyclic aromatic hydrocarbons (PAHs) by diverse strains, little would be known about the fate of polycyclic aromatic hydrocarbons (PAHs) in high salinity environments (Fathepure, B. Z. Recent studies in microbial degradation of petroleum hydrocarbons in hypersaline environments. The Proceedings from Halophiles 2013, the International Congress on Halophilic Microorganisms. Vol. 5. No. 12. Frontiers Media SA, 2015).

Despite many reports concerning the microbial degradation of aromatic compounds, degradation of aniline at high salt concentrations is still limited. Therefore, microorganisms which degrade or transform aniline in the presence of high salt concentrations when salt stress is superimposed on pollution stress are of great importance. In particular, means and methods for reducing the aniline content of hypersaline wastewaters are highly required.

The technical problem underlying the present invention can be seen as the provision of methods for complying with the aforementioned needs. The technical problem is solved by the embodiments characterized in the claims and herein below.

Advantageously, it has been found in the studies of the present invention that two halophilic microbial species, *Haloferax* sp. D1227 (ATCC 51408), and *Halomonas alimentaria* (DSM 15356) efficiently degrade aniline under conditions of high salinity. Further, it was shown that *Halomonas alimentaria* (DSM 15356) efficiently degrade formate. *Haloferax* sp. D1227 and *Halomonas* alimentaria are previously reported to grow on certain aromatic compounds, however, no study on aniline (or formate) degradation has been reported previously for the given strains. These cells actively degrade aniline from their hypersaline environment. These findings of the present invention can be applied to natural and industrial residual streams.

Accordingly, the present invention relates to a method for reducing the aniline content of a composition comprising hypersaline wastewater, said method comprising the steps of:

(a) providing a composition A comprising hypersaline wastewater and aniline, and (b) contacting composition A with cells of at least one halophilic microbial strain, thereby generating a composition B comprising said composition A and cells of said at least one halophilic microbial strain.

According to step (a) of the method of the present invention, a composition A comprising hypersaline wastewater shall be provided. Said composition A is a solution which comprises said hypersaline wastewater and aniline. The hypersaline wastewater is preferably industrial wastewater comprising aniline, in particular brine comprising aniline.

According to step (b) of the method of the present invention, composition A is contacted with cells of the at least one halophilic microbial strain. Thereby, a composition B is generated comprising composition A (and thus the hypersaline wastewater and aniline) and the at least one halophilic microbial strain (i.e. cells of this strain). In an embodiment of the method of the present invention, composition A is contacted with the cells by mixing composition A with the cells.

In accordance with the method of the present invention, it is envisaged that contacting composition A with the cells in step (b) does not significantly increase the volume of the resulting composition B (as compared to the volume of composition A). Accordingly, the main component of composition B shall be composition A. Thus, step (b) does not significantly dilute composition A. The dilution factor is preferably lower than 1.2, more preferably lower than 1.1, and most preferably lower than 1.05. Further, it is envisaged that the dilution factor is lower than 1.03 or 1.02. The term "dilution factor" as used herein preferably refers to ratio of the volume of composition B to the volume of composition A. In other words, composition B comprises (in particular consists of) at least 80%, more preferably at least 90%, and most preferably at least 95% by weight of composition A, based on the total volume of composition B. Further, it is envisaged that composition B comprises (in particular consists of) at least 97% or 98% by weight of composition A, based on the total volume of composition B. Since the dilution factor is negligible, it is envisaged that composition A comprises the same, or essentially the same content of aniline and NaCl (and, if present, the same or essentially the same content of formate) as composition B.

The hypersaline wastewater, and thus composition A and composition B shall comprise NaCl in a high concentration. A high concentration of NaCl as referred to herein is a concentration of least 2% (w/v), based on the total volume of the wastewater or the composition. The wastewater, composition A or B could comprise NaCl in a concentration up to the saturation concentration of NaCl since it has been shown in the studies underlying the present invention that the aniline content was reduced even at a NaCl concentration of 20.0% (w/v). Thus, the upper limit for the concentration is, in principle, the saturation concentration of NaCl.

Preferably, a high concentration of NaCl is a concentration of NaCl of at least 4% (w/v), more preferably of at least 6% (w/v), even more preferably of at least 8% (w/v), and most preferably of at least 10% (w/v) based on the total volume of composition or wastewater (e.g. of composition B). In a further preferred embodiment, a high concentration of NaCl is a concentration of at least 12.5% (w/v), in particular of at least 14% (w/v), based on the total volume of the composition or wastewater.

Although the upper limit for a high concentration of NaCl is, in principle, the saturation concentration of NaCl, it is envisaged that the wastewater, composition A or B comprises NaCl in a concentration of less than the saturation concentration. Preferably, the NaCl concentration in the wastewater, composition A, or composition B is less than 23% (w/v), more preferably less than 22% (w/v), even more preferably less than 20%, and most preferably less than 18% (w/v) NaCl, again based on the total volume of the composition or the wastewater. Thus, e.g. the concentration of NaCl may be at least 14% (w/v), in particular at least 16%, but less than 22% (w/v), in particular less than 20% (w/v), based on the total volume (of the wastewater, composition A, or composition B).

In an embodiment of the present invention, the wastewater or the composition A or B comprises NaCl in a concentration of more than 6% (w/v) based on the total volume of the wastewater, composition A, or composition B.

High concentrations of NaCl can be found in various industrial wastewaters. In a preferred embodiment, the hypersaline wastewater is derived from methylene diamine production as a preproduct of polyurethanes. Accordingly, step a) of the method of the present invention may comprise the isolation of hypersaline wastewater from methylene diamine production.

The hypersaline wastewater might have been subjected to previous steps. In an embodiment, the hypersaline wastewater has been subjected to a purification step with activated charcoal, thereby reducing the TOC content. Further, the wastewater might have been filtered. Further, it is envisaged that the NaCl concentration of the wastewater is concentrated prior to carrying out step a) of the method of the present invention. Preferred methods for concentrating a composition comprising NaCl are described elsewhere herein.

Advantageously, it has been shown in the context of the present invention that the microbial strains there were analyzed are capable of reducing the aniline content of hypersaline salt water. Thus, it is envisaged that composition A (and composition B) comprises aniline. Alternatively or additionally, composition A (and composition B) shall comprise formate as was shown that the strain $H.$ $alimenteria$ is capable of reducing the formate content of hypersaline wastewater as well. Thus, composition A (and composition B) may comprise aniline and/or formate, in particular aniline and formate.

Preferably, composition A and/or composition B comprises aniline in an amount of at least 0.5 mg/l, more preferably in an amount of at least 2 mg/l, and most preferably in an amount of at least 5 mg/l. Further, it is envisaged that composition A (or B) comprises aniline in an amount of at least 10 mg/l, more preferably in an amount of at least 20 ml/l.

More preferably, composition A and/or composition B comprises aniline in an amount of more than 2 mg/l but less than 200 mg/l. Even more preferably, composition A (or B) comprises aniline in an amount of at 2 mg/l but not more than 100 mg/l. Most preferably, composition A (or B) comprises aniline in an amount of at least 5 mg/l but not more than 80 mg/l. Further, it is envisaged that composition A and/or composition B comprise 0.5 to 12 mg/l aniline.

As set forth, the compositions as set forth in connection with the present invention may comprise formate, e.g. if the strain $H.$ $alimenteria$ is used. In this case, composition A and/or B, preferably, comprises formate in an amount of more than 25 mg/l, in particular in an amount of more than 50 mg/l. More preferably, composition A (and/or B) comprises formate in an amount of more than 50 mg/l but less than 2000 mg/l. Even more preferably, composition A (and/or B) comprises formate in an amount of more than 100 mg/l but less than 1000 mg/l. Most preferably, composition A (and/or B) comprises formate in an amount of more than 100 mg/l but less than 500 mg/l.

The hypersaline wastewater and thus composition A and composition B may comprise additional organic compounds such as phenolate and/or MDA (4,4'-Methylenedianiline). In an embodiment composition A (or composition B) 0.1 mg/l to 10 mg/l MDA, in particular 1 to 5 mg/l MDA, and/or 2 to 100 mg/l phenolate, in particular 5 to 20 mg/l phenolate.

Preferably, composition A has a total organic carbon ("TOC") content of more than 50 mg/l, more preferably of more than 60 mg/l, even more preferably of more than 60 mg/l, and most preferably of more than 65 mg/l. Further, it is envisaged that composition A has a TOC (total organic carbon) content of more than 70 mg/l, in particular of more than 70 mg/l. Preferably, the composition A can have a total organic carbon ("TOC") content of up to 1000 mg/l and more.

In accordance with the present invention, the aniline content of hypersaline wastewater and, optionally, the formate content, and thus the aniline and, optionally the formate content of composition A and composition B, respectively, shall be reduced. The term "reducing" as used herein shall refer to a significant reduction of the aniline content (and optionally the formate) content of the hypersaline wastewater (or of composition A or B). Preferably, the term denotes a decrease of the aniline and/or formate content (and optionally the formate content) of at least 30%, at least 50%, at least 70% or in particular of at least 90% or of at least 95% of the total aniline content present in the hypersaline wastewater, composition A or composition B, respectively.

Preferably, the treated wastewater comprises aniline in an amount of less than 5 mg/l, more preferably less of than 2 mg/l and most preferably less than 0.5 mg/l after the method of the present invention has been carried out. Also preferably, the treated wastewater comprises formate in an amount of less than 15 mg/l, more preferably less of than 10 mg/l and most preferably less than 5 mg/l after the method of the present invention has been carried out (in particular, if $H.$ $alimenteria$ has been used).

Further, it is envisaged that the aniline content (and optionally the formate content) is eliminated completely.

By carrying out the method of the present invention, the TOC content will be reduced as well (i.e. in addition to the aniline content and optionally the formate content). Preferably, the treated wastewater has a TOC content of less than 40 mg/l, more preferably of less than 30 mg/l and most preferably of less than 20 mg/l (in particular after separation of the cells as described herein elsewhere).

Preferably, the aniline content is reduced by the presence, and thus, by the activity of cells of the at least one halophilic microbial strain as referred to herein in connection with the present invention. The formate content is preferably reduced by the presence of *H. alimenteria*. Preferably, said the aniline content is reduced by degraded of said cell by said cells. A reduction of the concentration of aniline/formate by dilution of the wastewater/composition is not considered as a reduction of the aniline/formate content. Accordingly, the terms "reducing the aniline content" or "reducing the formate content" do not encompass the reduction of the concentration of the compound by dilution of composition A or B.

Preferably, the cells of at the least one halophilic microbial strain are *Halomonas alimentaria* (DSM 15356) cells and/or *Haloferax* sp. D1227 (ATCC 51408) cells. Further, envisaged are combinations, i.e. mixtures of the aforementioned cells. Thus, in an embodiment of the present invention, the cells are cells of the strain *Halomonas alimentaria*. In a further embodiment of the present invention, the cells are cells of the strain *Haloferax* sp. D1227.

All three strains are well known in the art. The strains are held in public collections and can be ordered without restriction:

The strain *Haloferax* sp. D1227 has been deposited in the ATTC (American Type Culture Collection, Manassas, Va., USA) under ATCC number 51408. "D1227" is the strain designation. The strain was e.g. described by Emerson D, et al. *Haloferax* sp. D1227, a halophilic Archaeon capable of growth on aromatic compounds. Arch. Microbiol. 161: 445-452, 1994. The document is herewith incorporated by reference in its entirety.

The strain *Halomonas alimentaria* has been deposited in the DSM (Deutsche Sammlung von Mikroorganismen und Zellkulturen, Braunschweig, Germany) under DSM number 15356. The strain was e.g. described by Yoon, J. H., Lee, K. C., Kho, Y. H., Kang, K. H., Kim, C. J., Park, Y. H. (2002). *Halomonas alimentaria* sp. nov., isolated from jeotgal, a traditional Korean fermented seafood. Int. J. Syst. Evol. Microbiol. 52: 123-130. The document is herewith incorporated by reference in its entirety. As set forth elsewhere herein, the strain *Halomonas alimentaria* is capable of reducing both the formate content and the aniline content of hypersaline wastewater. Thus, the hypersaline wastewater, composition A and/or composition B may comprise aniline or formate, or both aniline or formate.

How to culture these strains is well known in the art, e.g. culture conditions can be e.g. assessed from the ATCC and DSMZ databases. Preferred media compositions for the three strains are described in Example 1 of the Examples section.

The cells to be contacted with composition A (i.e. mixed with composition A) in step b) shall be viable, i.e. living cells. How to assess whether cells are viable, or not, can be assessed by wellknown methods. Of course, a certain percentage of the cells to be mixed with composition A might not be viable. However, this is taken into account by the skilled person.

In an embodiment, a suspension of cells of the at least one halophilic microbial strain is mixed with composition A. The cells are preferably derived from a pre-culture of cells of the respective strain. The suspension shall comprise a suitable substrate (i.e. a carbon source), although not necessary, the pre-culture of the cells can be been carried out in the presence of aniline (and optionally formate, in particular if *H. alimenteria* is used), i.e. the medium for the pre-culture might contain aniline (and optionally formate).

The amount of cells of the at least one halophilic microbial strain as referred to herein to be mixed, i.e. contacted with composition A, can be determined by the skilled person. The cell amount to be mixed shall allow for a sufficient reduction of the aniline content and/or of the formate content. The amount e.g. depends on the volume of composition A to be treated by the method of the present invention. In general, the larger the volume of composition A to be treated, the larger shall be the amount of cells to be used. This will be taken into account by the skilled person.

The mixing may take place in a suitable container. In an embodiment, the mixing is carried out in a bioreactor. The term "bioreactor" as used herein refers to a system in which conditions are closely controlled to permit the reduction of the aniline content (and/or of the formate content). In an embodiment, said bioreactor is a stirred tank reactor. Preferably, the bioreactor is made of a noncorrosive material such as stainless steel. The bioreactor can be of any size as long as it is useful for the incubation of composition B. Preferably, the bioreactor allows for a large scale reduction of the aniline (and/or formate) content of hypersaline wastewater. Therefore, it is envisaged that the bioreactor has a volume of at least 1, 10, 100, 500, 1000, 2500, or 5000 liters or any intermediate volume. However, it is also envisaged to carry out the method of the present invention at a low scale, such as with 5 to 100 ml of composition B.

Composition B may further comprise media components which allow for the reduction of the aniline content (and/or the formate content) by cells of the at least one halophilic microbial strain. Such media components are well known in the art and include e.g. $NH_4Cl$, $KH_2PO_4$, $Na_2SO_4$, $MgCl_2$ (e.g. $MgCl_2*6H_2O$), $FeCl_3$, $MgSO_4$, $CaCl_2$ (e.g. $CaCl_2*2 H_2O$), KBr and KCl. In an embodiment, composition B comprises a phosphor source, a nitrogen source, a sulfur source, a potassium source and/or a magnesium source (as media components). Composition B may further comprise trace elements such as iron, copper, zinc and cobalt. In an embodiment, the media components are added to composition B after contacting composition A with the cells, i.e. mixing the composition and the cells (as set forth in step (b)).

The selection of suitable media components can be carried out by the skilled person without further ado. Moreover, the skilled person can determine suitable concentrations of media components without further ado.

For example, the following concentration ranges and concentrations for the following media components are considered as suitable. The present invention is, however, not limited to the media components referred to above and the following concentration ranges.

Concentration in composition B:
$NH_4Cl$: 0.5 to 3 g/l, e.g. 1.5 g/l
$KH_2PO_4$: 0.05 to 0.5 g/l, e.g. 0.15 g/l
$MgC_2*6 H_2O$: 0.5 to 3 g/l, e.g. 1.1 g/l
$CaC_2*2 H_2O$: 0.1 to 2 g/l, e.g. 0.55 g/l
KCl: 0.5 to 3 g/l, e.g. 1.66 g/l
$Na_2SO_4$: 0.5 to 1 g/l, e.g. 0.75 g/l Further preferred concentrations for media components are specified in Table 1 of the Example 2 for *Haloferax* sp. D1227 and in Table 2 of Example 2 for *Halomonas alimentaria*.

In a preferred embodiment of the present invention, composition B further comprises a substrate. Said substrate shall allow for the growth of the at least one halophilic microbial strain. Whether a substrate allows for the growth of the strain, or not, can be assessed by the skilled person without further ado. For example, preferred substrates for *H. alimenteria* are listed in table 1 of Wang et al. (International Journal of Systematic and Evolutionary Microbiology (2007), 57(6), 1222-1226) which herewith is incorporated by reference in its entirety.

The substrate shall be present in addition to aniline (and/or formate). Preferably, the presence of an additional substrate (i.e. in addition to aniline (and/or formate)) allows for an improved reduction of the aniline content (and/or the formate content).

The substrate is preferably added to composition B. Preferably, said substrate is a carbohydrate (that allows for the growth of the strain), more preferably said substrate is an organic acid or a sugar (that allows for the growth of the strain), more preferably the substrate is selected from glycerol, acetate, glucose, sucrose, lactate, malate, succinate, and citrate. In a particular preferred embodiment, the substrate is glycerol.

Preferably, composition B comprises a substrate if the incubation is carried out as continuous process. The substrate shall allow for biomass growth in slow rate in order to achieve stability of degradation in continuous mode. Advantageously, it was observed that the content of aniline could be continuously degraded once cells are growing at their maximum growth rates, when a further substrate, glycerol, was continuously added to composition B, i.e. a reactor containing composition B.

Suitable concentrations or concentration ranges for the substrate can be determined by the skilled person without further ado. The reduction of the aniline content (and/or the reduction of the formate content) and thus the incubation as referred to herein is preferably done under carbon limitation. Accordingly, it is envisaged that the concentration of the substrate such as growths allows for biomass growth at a slow rate. Thereby fresh biomass is produced which allows for the reduction of the aniline (and/or the formate) content in a continuous way. Preferably, the substrate is added to composition B in an amount that is completely taken up by the cells. Thus, it is envisaged that the TOC content would not be increased by the addition of the substrate.

For example, it is envisaged that the concentration of the substrate, in particular of the substrates mentioned above, in composition B is 0.5 g/l to 10 g/l, in particular 0.5 g/l to 5 g/l.

In an embodiment of the present invention, the further media components and/or the suitable substrate are (is) added to composition B, in particular after mixing composition A and the cells of the at least one halophilic microbial strain. E.g. the further media components and/or the suitable substrate can be at the beginning of the incubation of composition B or during incubation of composition B (e.g. continuously or as pulse).

Of course, the concentration of the substrate will change during incubation, because the substrate will be metabolized by the cells comprised by composition B at a certain rate. Thus, the substrate concentration might not be constant. Nevertheless, additional substrate might be added during incubation in order to compensate for the decrease of the substrate content.

After contacting composition A with the cells, the resulting composition B is incubated in order to allow for the reduction of the aniline (and/or the formate) content by the cells of at said at least one halophilic microbial strain. Accordingly, the method of the present invention preferably comprises the further step (c) of incubating composition B. In this incubation step, the aniline (and/or the formate) content is reduced.

Accordingly, the present invention in particular envisages a method for reducing the aniline content (and/or the formate content) of a composition comprising hypersaline wastewater, said method comprising the steps of:

(a) providing a composition A comprising hypersaline wastewater and aniline, (b) contacting composition A with cells of at least one halophilic microbial strain, thereby generating a composition B comprising said composition A and cells of said at least one halophilic microbial strain, and (c) incubating composition B, thereby reducing the aniline (and/or formate) content of the composition.

The incubation of composition B shall be carried out under suitable conditions, i.e. under conditions which allow for the reduction of the aniline/formate content by the cells of said at least one halophilic microbial strain as referred to herein. Preferably, the incubation is carried out in a bioreactor.

Preferably, the induction of composition B (and thus reduction of the aniline/formate content) is carried out at temperature of 18° C. to 45° C., more preferably at a temperature of 20° C. to 40° C., and most preferably at a temperature of 20° C. to 35° C.

It is envisaged that the reduction is carried out at a constant temperature. However, it is also contemplated that the temperature might change during the incubation. In a preferred embodiment of the present invention, the temperature of composition B is monitored during incubation.

In a preferred embodiment of the method of the present invention, composition B is agitated (during incubation). Preferably, composition B is agitated in the range of 100 rpm to 700 rpm, more preferably in the range of 100 rpm to 500 rpm, and most preferably in the range of 200 rpm to 400 rpm.

The incubation is carried out under aerobic conditions. Preferably, aerobic conditions are maintained by adding air or purified oxygen to composition B continuously.

Preferably, composition B has a pH value in the range of 5.8 to 8.5, more preferably 6.0 to 8.0, and most preferably in the range of 6.2 to 7.5. Accordingly, the incubation is preferably carried out at a pH value in the range of 5.8 to 8.5, preferably in the range of 6.2 to 7.5. In a preferred embodiment, the pH value of composition B is monitored during incubation. It is envisaged that the pH value is kept constant during cultivation. This can be e.g. achieved by adding HCl.

The optimal temperature ranges and pH value ranges may depend on the halophilic strain that is used for the reduction of the aniline/formate content.

If cells of *Halomonas alimentaria* are used, the incubation is preferably carried out at a pH value of composition B in the range of 6.5 to 8.5, in particular in the range of 6.5 to 7.4. Moreover, it is envisaged that the incubation is preferably carried out at a temperature of 20° C. to 37° C., more preferably at a temperature of 25° C. to 35° C. The temperature optimum is about 30° C.

If cells of *Haloferax* sp. D1227 are used, the incubation is preferably carried out at a pH value of composition B in the range of 6.5 to 8.0, in particular in the range of 6.8 to 7.5. Moreover, it is envisaged that the incubation is preferably carried out at a temperature of 20° C. to 40° C., more preferably at a temperature of 25° C. to 37° C. The temperature optimum is about 35° C.

The concentration of the biomass, i.e. of cells of the at least one halophilic microbial strain, in the incubation step can be any concentration that allows for the reduction of the aniline content (and/or for the reduction of the formate content). For example, the biomass concentration can be in a range between 0.2 and 10 g/l, in particular in a range between 0.5 to 4.5 g/l. Optimum biomass concentration for 250 mg/l aniline is 1.6 g/l. Thus, it is also envisaged that the biomass concentration is in a range between 1.3 to 1.9 g/l.

As set forth above, the method of the present invention is preferably carried out in a large scale. Accordingly, composition B has preferably a volume of at least 1, 10, 100, 500, 1000, 2500, or 5000 liters or any intermediate volume. However, smaller volumes such as volumes of at least 5 ml or 100 ml are envisaged by the present invention as well (e.g. for tests).

The method of the present invention, in particular the incubation as referred to herein in step (c) of the method of the present invention, is preferably carried out as a batch, fed-batch or continuous process, in particular as batch, fed-batch or continuous process with cell retention (preferably in a bioreactor). Accordingly, composition B is incubated under batch, fed-batch, or continuous conditions. The term "batch process" preferably refers to a method of incubating cells in which all the components that will ultimately be used for incubating the cells including the substrate and the further media components, composition A as well as the cells themselves, are provided at the initiation of the incubation process. A batch process is preferably stopped at some point and the treated hypersaline wastewater is isolated. The term "fed-batch process" as used herein refers to a process of incubating cells in which additional components such as the additional media components and/or the substrate are provided to the culture at some time after the initiation of the culture process. The A fed-batch culture is preferably stopped at some point and the cells and/or components in the medium are harvested and the treated hypersaline wastewater is isolated.

In a particularly preferred embodiment, the method of the present invention, and thus the incubation as referred to herein, is carried in continuous culture with a mixed feed system using a substrate as referred to above (such as glycerol or acetate).

In a preferred embodiment of the aforementioned method of the present invention, the method further comprises the step of separating the cells of the at least one halophilic microbial strain from the composition B, thereby giving a composition C. The separation of the cells from composition B shall be carried out after the incubation of composition B, i.e. after the reduction of the aniline (and/or formate) content, as step (d).

The resulting composition C (which is herein also referred to as the "treated wastewater") shall be essentially free of cells of the at least one halophilic microbial strain. In other words, composition C shall not comprise the cells.

The separation of cells from composition B can be achieved by all cell retention means that are deemed appropriate. For example, the separation of cells can be achieved by centrifugation, filtration, or by decanting. Preferably, the cells are separated from composition B by filtration.

Further, the cells could be immobilized on beads or a solid support, thereby allowing the separation of the cells from composition B.

If a continuous process is carried out, it is contemplated that the separated cells are fed back to the wastewater. Accordingly, the separated cells are contacted with composition A or, in particular composition B.

If the method is carried out in a bioreactor, the bioreactor preferably comprises means for cell retention. Preferably, the bioreactor comprises a membrane suitable for separating the cells from composition B by filtration.

The resulting composition C, i.e. the treated wastewater, preferably comprises aniline in an amount of less than 5 mg/l. More preferably, it comprises aniline in an amount of less than 2 mg/l and most preferably less than 1 mg/l. Also preferably, the treated wastewater comprises formate in an amount of less than 15 mg/l, more preferably less of than 10 mg/l and most preferably less than 5 mg/l after the method of the present invention has been carried out (in particular if the strain *H. alimenteria* is used).

Further, composition C preferably has a TOC content of less than 40 mg/l, more preferably of less than 30 mg/l and most preferably of less than 20 mg/l.

In a preferred embodiment of the present invention, the method further comprises concentrating the composition C, thereby giving a composition C*.

This step will increase the NaCl concentration of the treated wastewater, i.e. the NaCl is up-concentrated in the composition. Preferably, the concentrated composition C* comprises NaCl in a concentration of more than 20.0% (w/v), based on the total volume of composition A, in particular in a concentration of more than 22% (w/v). These NaCl concentrations are ideal concentrations when used in the feed stream of the chloralkali process.

In accordance with the present invention, the up-concentration of composition C can be concentration by any method deemed appropriate. Preferred methods are reverse osmosis, ultraftltration and nanofiltration. In these methods, a positive osmotic pressure to one side of a filtration membrane. Further, the up-concentration can be achieved by vaporization.

As set forth above, composition A and B may comprise NaCl in a concentration of more than 20% (w/v). If these concentrations are used, the concentration step, in principle, could be omitted when subjecting the treated wastewater to the chloralkali process.

The definitions and explanations given herein above apply mutatis mutandis to the following subject-matter of the present invention, in particular to the following method of the present invention for the production of chlorine and/or sodium hydroxide, to the composition of the present invention, the bioreactor of the present invention, and the use of the present invention.

The present invention also relates to a method for the production of chlorine and sodium hydroxide, comprising the steps of
 (i) providing a composition C according to the method of the present invention or a composition C* according to the method of the present invention, and
 (ii) subjecting the composition according to (a) to a sodium chloride electrolysis, thereby producing chlorine and sodium hydroxide.

Step (i) of the aforementioned method, i.e. the provision of a composition C according to the method of the present invention or of a composition C* according to the method of the present invention, preferably comprises the steps of the method for reducing the aniline content of a hypersaline solution.

In an embodiment, composition C is provided by the following steps.
(a) providing a composition A comprising hypersaline wastewater and aniline and/or formate,
(b) contacting composition A with cells of at least one halophilic microbial strain, thereby generating a composition B comprising said composition A and cells of said at least one halophilic microbial strain,
(c) incubating composition B, thereby reducing the aniline content and/or the formate content of the composition, and
(d) separating the cells of the at least one halophilic microbial strain from composition B, thereby providing composition C.

If composition C* provided, step ii) preferably comprises the further step of (e) concentrating the composition C, thereby providing composition C*.

The electrolysis of sodium chloride can be carried out by methods well known in the art. Preferably, the electrolysis is membrane cell electrolysis of sodium chloride, in particular membrane electrolysis using oxygen consuming electrodes, diaphragm cell electrolysis of sodium chloride or mercury cell electrolysis of sodium chloride.

The present invention further concerns the composition B as defined herein above in connection of the method of the present invention. Accordingly, the present invention relates to the composition B comprising hypersaline wastewater and further comprising aniline (and/or formate as described elsewhere herein), and cells of at least one halophilic microbial strain. Said composition shall also comprise NaCl.

Preferred contents of aniline and/or and further preferred NaCl concentrations are disclosed in connection of the method of the present invention for reducing the aniline and/or the formate content.

In addition, the composition may comprise components (such as further media components and/or a suitable substrate, phenol, aniline etc.) as described above. Preferred formate concentrations are also described elsewhere.

Further, the present invention relates to a bioreactor comprising at least 1 l of the composition B of the present invention.

Further, the present invention relates to the use of cells of at least one halophilic microbial strain as set forth herein for reducing the aniline content (and/or the formate content) of hypersaline wastewater or of a composition A or B comprising said wastewater. In particular, the present invention relates to the use of cells of the at least one halophilic microbial strain for reducing the aniline content (and/or the formate content) of a composition B, or in particular of composition A as referred to herein.

The definitions and explanations given herein above in connection with the method of the present invention of reducing the aniline content (and/or formate content) apply accordingly to aforementioned uses. Thus, in accordance with the aforementioned uses, the aniline content (and/or the formate content) is preferably reduced as described herein above in connection with the method of the present invention.

The Figures show:
FIG. 1 Graph shows aniline reduction by strain *Halomonas alimentaria* at NaCl concentration of 15% w/v in synthetic media containing 10 and 20 mg/l aniline. Biomass was reduced and aniline was degraded. In presence of a second substrate 50 mg/l phenol still no increase in biomass concentration occurred.

Figure 2:
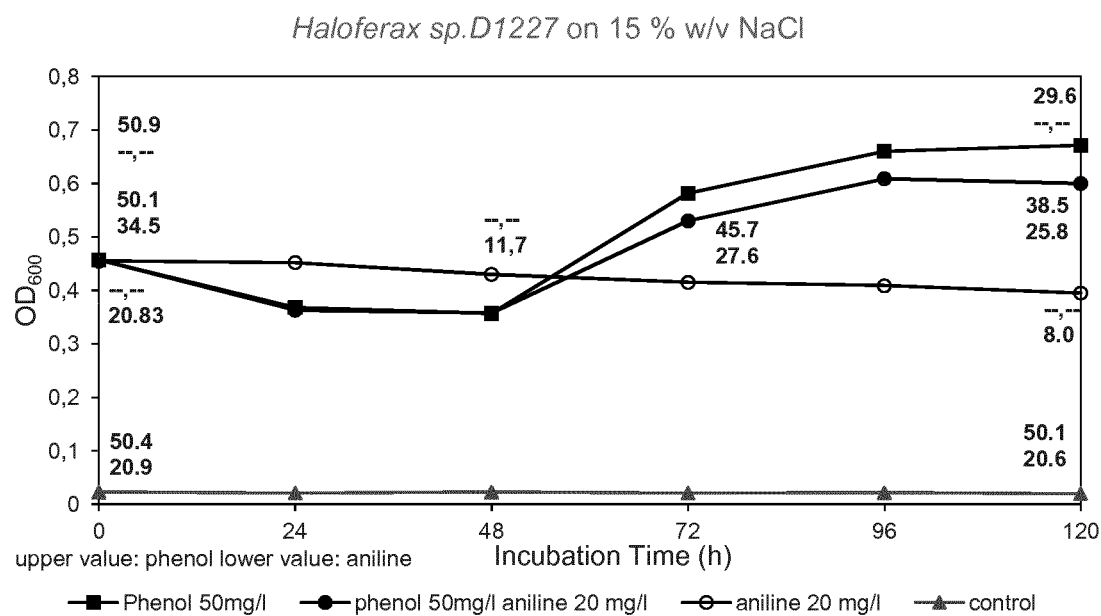

FIG. 2 Shows aniline degradation by strain *Haloferax* sp. D1227 in synthetic media containing 15% w/v NaCl and 20 mg/l aniline. 50% of Aniline is degraded after 48 hours of incubation. Reduction in optical density at 600 nm is shown. In presence of a second substrate 50 mg/l phenol increase in biomass concentration as well as reduction in phenol and aniline is detected.

Figure 3:
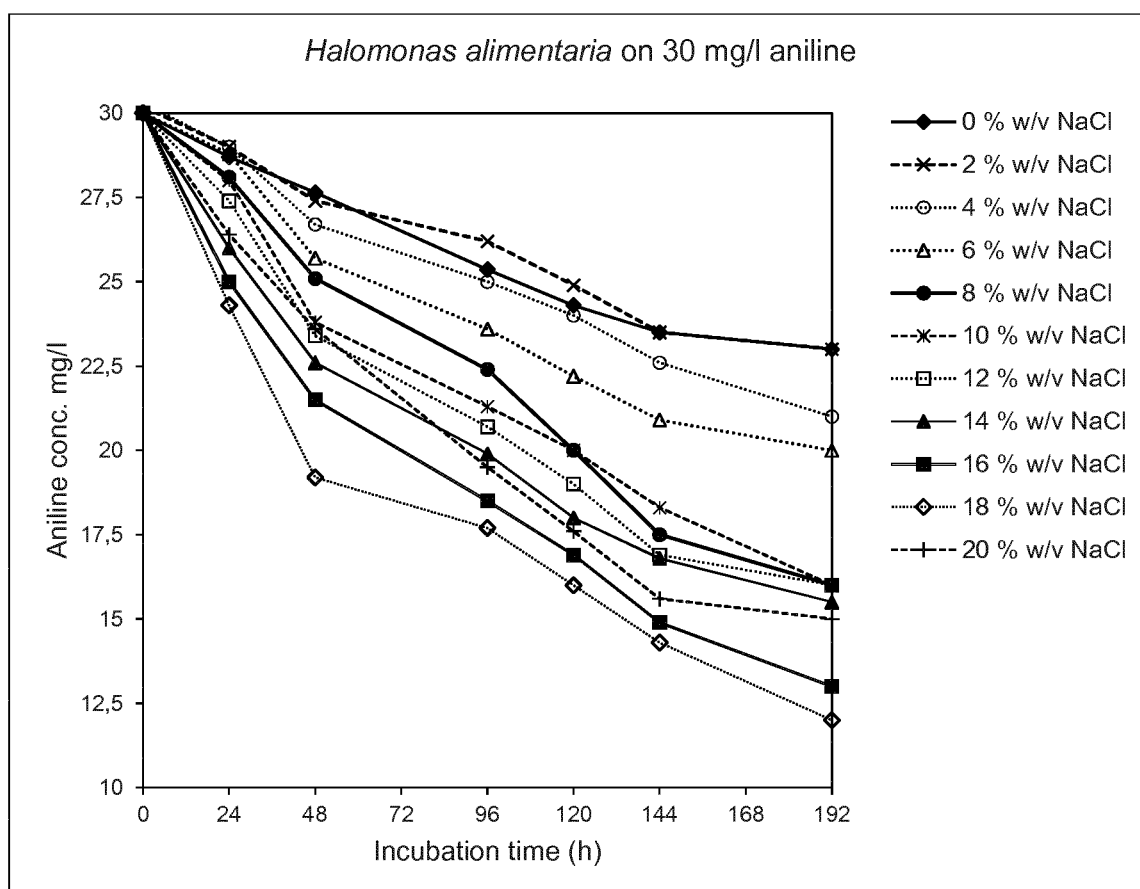

FIG. 3 Aniline degradation at various salt concentrations (0 to 20% w/v NaCl) using cells of halotolerant bacteria *Halomonas alimentaria*. Rate of aniline degradation is higher at higher salt concentrations. Best aniline degradation occurs at NaCl concentration of 18% w/v.

Figure 4:
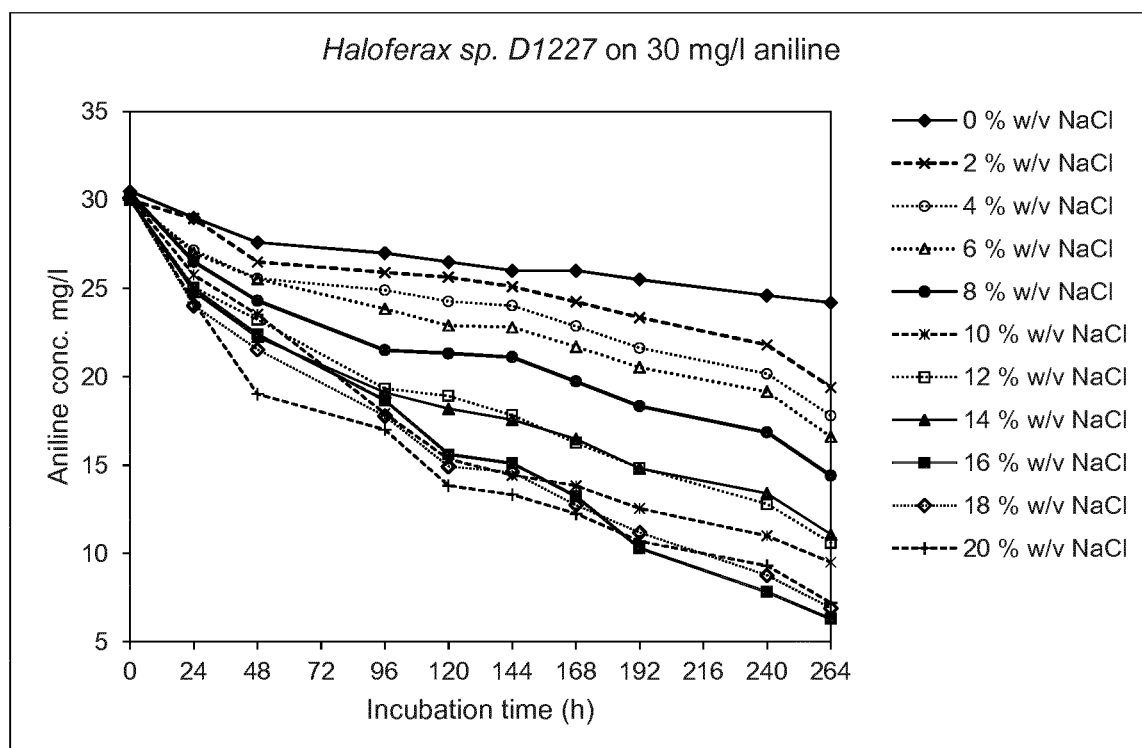

FIG. 4 The graph illustrates aniline degradation at various salt concentrations (0 to 20% w/v NaCl) using cells of halophilic bacteria *Haloferax* sp. D1227. Rate of aniline degradation is higher at higher salt concentrations. Best aniline degradation occurs at NaCl concentration of >14% w/v.

Figure 5:
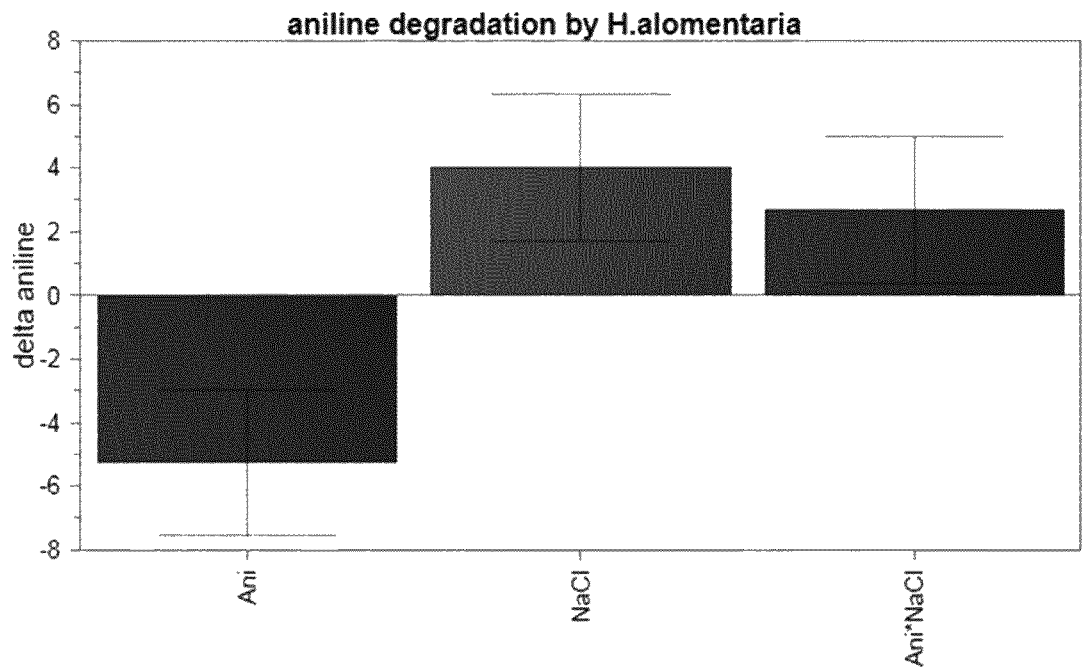

FIG. 5 The coefficient plot shows significance of two factors initial aniline concentration and NaCl concentration on aniline degradation for strain *Halomonas alimentaria*. At lower salt and aniline concentration better removal can be observed. pH seem to have no significance on aniline removal. Aniline degradation by *H. alimentaria* occurs at all NaCl concentrations.

Figure 6:
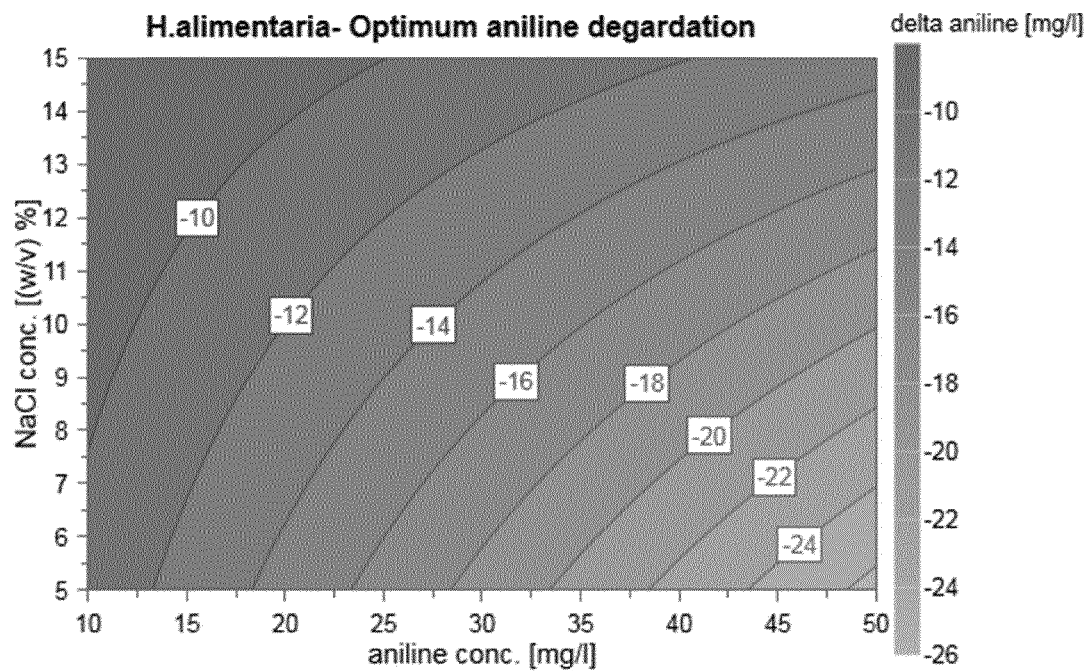

FIG. 6 The response counter plot shows the optimal aniline degradation may occur at lower initial aniline concentrations and lower NaCl concentrations for the strain *Halomonas alimentaria*.

Figure 7:
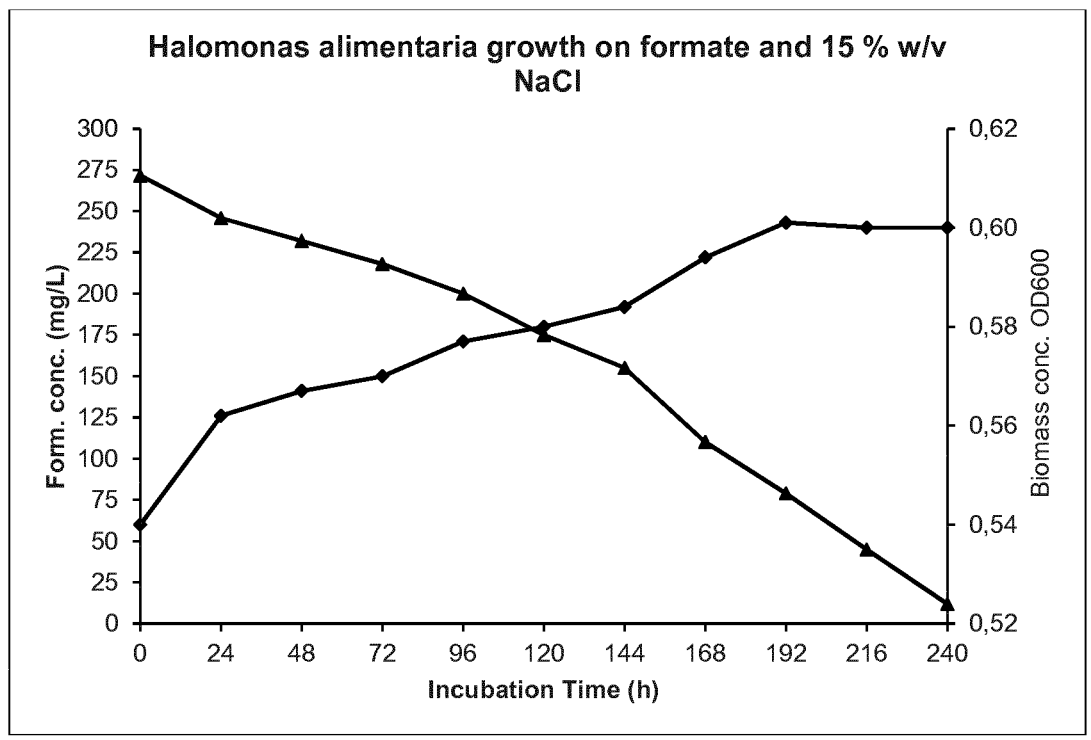

FIG. 7 Shows formate uptake by strain *Halomonas alimentaria* on an industrial residual media containing 15% w/v NaCl. Formate is reduced and biomass increases over time.

All references cited in this specification are herewith incorporated by reference with respect to their entire disclosure content and the disclosure content specifically mentioned in this specification.

The invention will be merely illustrated by the following Examples. The said Examples shall, whatsoever, not be construed in a manner limiting the scope of the invention.

EXAMPLES

Example 1: Aniline Degradation in Shake Flask Experiments

Strains and Media

*Halomonas alimentaria* (DSM 15356) (in this study *H. alimentaria*) wild type was purchased from dsmz. Shake-flask cultures for inoculum preparation were grown under 120 rpm and 30° C. in laboratory incubator (Infors, Switzerland) on media no. 514 suggested by dsmz with some modifications and following compositions (g/l): Yeast extract 5.0, Fe (III) citrate 0.1, NaCl 19.45, $MgCl_2$ 5.9, $Na_2SO_4$ 3.24, $CaCl_2$ 1.80, KCl 0.55, $NaHCO_3$ 0.16, KBr 0.08 and trace elements in mg/l $SrCl_2$ 34.0, $H_3BO_3$ 22.0, Na-Silicate 4.0, NaF 2.40, $(NH_4)NO_3$ 1.60, $Na_2HPO_4$ 8.0; pH 7.6.

*Haloferax* sp. D1227 (ATCC 51408) (in this study D1227) was purchased from American type culture collection. Shake-flask cultures for inoculum preparation were grown under 170 rpm and 35° C. with following media compositions (g/l): $(NH_4)_2SO_4$ 0.33, KCl 6.0, $MgCl_2.6H_2O$ 12.1, $MgSO_4 \cdot 7H_2O$ 14.8, $KH_2PO_4$ 0.34, $CaCl_2 \cdot 2H_2O$ 0.36, NaCl 100.0, Yeast extract 3.0, Tryptone 3.0; pH 6.8.

Analytics

Turbidity as indicator for cell growth was measured using Shimadzu UV/Vis spectrophotometer at 600 nm in 12 hour intervals. Residual aniline concentration in the culture supernatant was measured using HPLC. The HPLC (Thermo-Fisher) method was performed with an Acclaim PA C-16-3 μm column (Thermo-Fisher). Acetonitrile, 25 mM $KH_2PO_4$ pH 3.5 and MQ were used as the mobile phase and detection was done with UV at 190 nm. With an injection volume of 5 μl the limit of quantification for aniline is 1 ppm. Lower concentrations of aniline were also detectable.

Aniline Uptake Studies in Shake Flask

For the aniline uptake studies synthetically defined media was prepared for every strain. The media composition are listed below:

TABLE 1

Synthetic defined media (top table) and trace elements (bottom table) composition for strain *Haloferax* sp. D1227

| Composition | Amount g/l |
|---|---|
| NaCl | 140 |
| $NH_4Cl$ | 1.50 |
| $KH_2PO_4$ | 0.15 |
| $FeCl_3$ | 0.005 |
| $MgCl_2 \cdot 6H_2O$ | 1.30 |
| $MgSO_4 \cdot 7H_2O$ | 1.10 |
| $CaCl_2 \cdot 2H_2O$ | 0.55 |
| KCl | 1.66 |
| $NaHCO_3$ | 0.20 |
| KBr | 0.50 |
| $MnCl_2 \cdot 4H_2O$ | 0.003 |
| Trace elements | 1 ml |
| Aniline 99% | 5-100 mg |

| Composition | Amount mg/100 ml |
|---|---|
| $FeSO_4 \cdot 7H_2O$ | 136 |
| $CuSO_4 \cdot 5H_2O$ | 100 |
| $MnCl_2 \cdot 4H_2O$ | 50 |
| $CoCl_2 \cdot 2H_2O$ | 44 |
| $ZnSO_4 \cdot 7H_2O$ | 86 |

TABLE 2

Synthetic defined media composition for the strain *Halomonas alimentaria*

| Composition | Amount g/l |
|---|---|
| NaCl | 140 |
| $MgCl_2$ | 5.90 |
| $Na_2SO_4$ | 3.24 |
| $CaCl_2$ | 1.80 |
| KCl | 0.55 |
| KBr | 0.08 |
| $SrCl_2$ | 34 mg |
| $H_3BO_3$ | 22 mg |
| Na-Silicate | 4.0 mg |
| NaF | 2.4 mg |
| $(NH_4)NO_3$ | 1.6 mg |
| $Na_2HPO_4$ | 8.0 mg |
| Aniline 99% | 5-100 mg |

The strains were individually studied to check aniline uptake. Cells previously grown on the complex media were harvested by centrifugation at 3000 rpm, for 5 minutes. Cells were washed and dissolved in 500 ml shake-flasks containing 100 ml of their respective synthetic defined media and 15% w/v NaCl with aniline as only carbon source and were incubated at the respective temperature and agitation mentioned previously. The zero hour $OD_{600}$ was measured and one ml sample was stored for HPLC analysis as zero hour reference. Growth on aniline and the residual aniline concentration was monitored. The strains D1227 and *H. alimentaria* used in this study fail to use aniline as a source for growth, however, the residual aniline concentration over time showed that aniline was completely removed from the culture media both on synthetic media and on actual brine depending on initial aniline concentration. In presence of a second substrate in this case phenol 50 to 100 mg/l for D.1227 increase in biomass concentration and better aniline degradation was detected. The degradation of aniline was investigated in more details in more experiments in shake flasks as well as bioreactor in order to be able to control other process parameters.

Example 2: Optimum Culture Conditions for Aniline Degradation

Aniline Studies Using Multivariate Design of Experiments

In order to find the optimum conditions for aniline degradation by halophilic strain *Halomonas alimentaria* multivariate approach for design of experiments was used.

For the strain *H. alimentaria* a fractional factorial design of experiment was carried out to evaluate the influence of three factors (pH, initial aniline concentration and NaCl concentration) on three parameters (delta biomass, residual aniline concentration and delta pH). The factors and their ranges studied are given in the following table 3:

TABLE 3

The factors and responses studied for aniline degradation by *H. alimentaria*

| Factor name | Ranges |
|---|---|
| pH | 6.5 to 8.5 |
| aniline concentration | 10 to 50 mg/l |
| NaCl | 5 to 15% w/v |

The experiments were performed in the shake flasks at 30° C. and 120 rpm strokes. Increase in biomass concentration, pH changes and the residual aniline concentration were determined at 24 hour intervals. The measurements obtained after 144 hours were analyzed by Modde (statistical tool).

In case of *H. alimentaria* better aniline degradation was observed at lower NaCl concentrations of 5 and 10% w/v and lower pH and aniline concentration of 10 mg/l respectively.

Example 3: Aniline Degradation at Various Salt Concentrations

Degradation of aniline was studied for three different strains at various salt concentrations of 0 to 20% w/v in synthetic media containing 30 mg/l aniline as carbon source in shake flask experiments. The residual aniline concentration was determined by HPLC at 24 hour intervals. For the strain D1227 better aniline degradation occurred at NaCl concentrations of above 10% where the best degradation was at 16% w/v NaCl. For the strain *H. alimentaria* best aniline degradation was 70% of total aniline content at 18% w/v NaCl after 192 hours of incubation.

Example 4: Formate Removal Experiment by *Halomonas alimentaria* in Shake Flask Formate studies were done on an actual brine containing 15% w/v NaCl and 270 mg/l formate. For this experiment cells were previously grown on complex media (composition given in Example 1 strain and media section) at 30° C. with 120 rpm strokes. Cells from their late exponential growth phase were harvested by centrifugation for 5 minutes at 3000 rpm and 25 OC. Cells were washed and re-suspended in the brine with formate as only carbon source and media components given in Table 2; pH 7.2. Biomass concentration at zero hour was determined spectrophotometrically and the initial formate concentration was determined by HPLC. Residual formate concentration and biomass concentration were determined at 24 hour intervals. The results obtained showed slight increase in biomass concentration along with formate reduction over time. The results obtained suggest formate was removed and slight biomass increase was detected on formate as only substrate.

Example 5: Formate Degradation by *Haloferax* sp. D1227

A multivariate design of experiment approach was chosen to check formate uptake by *Haloferax* sp. D1227. Influence of two factors formate concentration and NaCl concentration (see table 4) was studied on formate uptake and biomass concentration. Experiments were performed in shake flasks on synthetic media with formate as only substrate and media components given in Example 1 at pH 6.8, temperature 35° C. and 150 rpm strokes. Residual formate concentration and biomass were determined in 24 hour intervals. HPLC results obtained up to 168 hours of incubation suggest formate stayed intact during the experiment and biomass showed decrease in all experiments. It could be concluded that formate is neither degraded by *Haloferax* sp. D1227 nor taken up by these cells as energy source. In table 5 list of the halophilic and halotolerant strains which we have studied for formate degradation are given.

TABLE 4

| Factor name | Studied range |
| --- | --- |
| NaCl concentration | 10 to 20% w/v |
| Formate concentration | 0.25 to 1 g/l |

TABLE 5

| Strain name | Formate degradation | NaCl concentration % w/v |
| --- | --- | --- |
| *Halomonas alimentaria* DSM 514 | Yes | 2 to 20 |
| *Haloferax* sp. D1227 ATCC | No | Non |
| *Natronobacterium gregoryi* DSM 3393 | No | Non |
| *Halobacterium salinarum* DSM 669 | No | Non |
| *Haloferax Volcanii* DSM | No | Non |

Example 6: Aniline Degradation in Additional Shake Flask Experiments

Additional halophilic and halotolerant strains were studied for Aniline degradation at various salt concentrations. The results are shown in the following table 6.

TABLE 6

Halophilic and halotolerant strains studied for Aniline degradation

| Strain name | Aniline degradation | NaCl conc. Ranges % w/v |
| --- | --- | --- |
| *Halomonas alimentaria* DSM 514 | Yes | about 2 to 20% |
| *Haloferax* D.1227 ATCC 51408 | Yes | about 2 to 25% |
| *Halobacterium salinarum* DSM 669 | No | — |
| *Natronobacterium gregoryi* DSM 3393 | No | — |

SUMMARY—CONCLUSIONS

Hypersaline wastewaters frequently comprise aniline and formate.

Aniline is the major industrial chemical intermediate which is used in the manufacturing of herbicides, developers, perfumes, medicine, rubber and dyes. Several physical and chemical methods, for example adsorption, ozonation and electrochemical treatment, are used to treat aniline-containing salty residual streams. Most of the mentioned treatments are not able to reduce the total organic carbon content in the salty residual streams down to the required maximum level.

In this invention, it was discovered that *Halomonas alimentaria* cells can degrade aniline from hypersaline environments. Further, it was discovered that *Halomonas alimentaria* cells and *Haloferax* sp. D1227 can degrade aniline and formate from hypersaline environments. This invention can be directed to optimal and efficient treatment of any hypersaline water containing aniline intending to reduce the total organic carbon content.

The other aspect of this current invention comprises the concept of residual to value. On one hand the environmental issues caused by highly saline residual streams enriched with considerable amount of unwanted organic contaminants and on the other hand need for high quality saline water as precursor for other industrial processes, such as membrane electrolysis, make the pretreatments of these hypersaline residual streams, absolutely crucial. The invention helps achieving this cheap, quick and efficient pretreatment to meet the requirement for membrane electrolysis to produce chlorine and/or sodium hydroxide.

The invention claimed is:

1. A method for reducing the aniline content of a composition comprising hypersaline wastewater, said method comprising the steps of:
    (a) providing a composition A comprising hypersaline wastewater and aniline, and
    (b) contacting composition A with cells of at least one halophilic microbial strain, selected from *Halomonas alimentaria* cells and/or *Haloferax* sp. D1227 cells, thereby generating a composition B comprising said composition A and cells of said at least one halophilic microbial strain, wherein said composition B comprises NaCl in a concentration of more than 6% (w/v), and
    (c) incubating composition B, thereby reducing the aniline content of the composition.

2. The method of claim 1, wherein said composition B comprises NaCl in a concentration of at least 8% (w/v).

3. The method of claim 1, wherein said composition B comprises NaCl in a concentration of a least 10% (w/v).

4. The method of claim 1, wherein the aniline content of the composition B comprises at least 0.5 mg/l aniline.

5. The method of claim 1, wherein the step (a) comprises isolating the hypersaline wastewater from methylene diamine production.

6. The method of claim 1, wherein said composition B further comprises a substrate that allows for the growth of the cells of at the least one halophilic microbial strain.

7. The method of claim 1, wherein the incubation in step (c) is carried out at temperature of 18° C. to 45° C. and/or wherein the incubation in step (c) is carried out at a pH value in the range of 5.8 to 8.5.

8. The method of claim 1, wherein said incubation in step (c) is carried out under aerobic conditions.

9. The method of claim 1, wherein composition B further comprises formate.

10. The method of claim 1, wherein said method further comprises the separation of the cells of the at least one halophilic microbial strain from composition B, thereby giving composition C, and optionally wherein the method further comprises concentrating composition C, thereby giving composition C.

11. A method for the production of chlorine and sodium hydroxide, comprising the steps of
  (i) providing a composition C or C* according to the method of claim 10, and
  (ii) subjecting the composition according to (a) to a sodium chloride electrolysis process, thereby producing chlorine and sodium hydroxide.

12. The method of claim 11, wherein the sodium chloride electrolysis is selected from membrane cell electrolysis of sodium chloride.

13. A composition B comprising hypersaline wastewater, aniline, and cells of at least one halophilic microbial strain, selected from *Halomonas alimentaria* cells and/or *Haloferax* sp. D1227 cells, wherein said composition B comprises NaCl in a concentration of more than 6% (w/v).

14. The method of claim 1, wherein said composition B comprises NaCl in a concentration of a least 12% (w/v).

15. The method of claim 1 wherein the aniline content of the composition B comprises at least 5 mg/l aniline.

16. The method of claim 1, wherein said composition B further comprises a substrate that allows for the growth of the cells of at the least one halophilic microbial strain, wherein the substrate is a carbohydrate.

17. The method of claim 1, wherein said composition B further comprises a substrate that allows for the growth of the cells of at the least one halophilic microbial strain, wherein the substrate is selected from the group consisting of glycerol, acetate, glucose, sucrose, lactate, malate, succinate, and citrate.

18. The method of claim 11, wherein the sodium chloride electrolysis is membrane electrolysis using oxygen consuming electrodes, diaphragm cell electrolysis of sodium chloride and mercury cell electrolysis of sodium chloride.

* * * * *